United States Patent [19]
Buendgen

[11] Patent Number: 5,763,754
[45] Date of Patent: Jun. 9, 1998

[54] INBRED CORN LINE ZS01219

[75] Inventor: Mike Buendgen, Madison, Wis.

[73] Assignee: Garst Seed Company, Slater, Iowa

[21] Appl. No.: 626,798

[22] Filed: Apr. 3, 1996

[51] Int. Cl.$^6$ .............................. A01H 5/00; A01H 4/00; A01H 1/00; C12N 5/04

[52] U.S. Cl. ............... 800/200; 800/250; 800/DIG. 56; 47/58; 47/DIG. 1; 435/412; 435/424; 435/430; 435/430.1

[58] Field of Search ................................. 800/200, 205, 800/250, DIG. 56; 47/58; 435/172.3, 172.1, 240.4, 145.47, 149.5, 412, 424, 430, 430.1

[56] References Cited

PUBLICATIONS

Coe, E.H., Jr. and M.G. Neuffer. The Genetics of Corn, p. 111.
Conger, B.V., F.J. Novak, R. Afza, and K. Erdelsky. "Somatic embryogenesis from cultured leaf segments of Zea mays". Plant Cell Reports, 6:345–347 (1987).
Duncan, D.R., M.E. Williams, B.E. Zehr and J.M. Widholm. "The production of callus capable of plant regeneration from immature embryos of numerous Zea mays genotypes", Planta, 165:322–332 (1985).
Edallo, et al., "Chromosomal Variation and Frequency of Spontaneous Mutation Associated with in Vitro Culture and Plant Regeneration in Maize" Maydica XXVI, pp. 39–56 (1981).
Forsberg, R.A. and R.R. Smith. "Sources, Maintenance, and Utilization of Parental Material", Hybridization of Crop Plants, Chapter 4, pp. 65–81 (1980).
Green, C.E. and R.L. Phillips. "Plant Regeneration from Tissue Cultures of Maize", Crop Science, vol. 15, pp. 417–421 (1975).
Green, C.E. and C.A. Rhodes. "Plant Regeneration in Tissue Cultures of Maize", Maize for Biological Research, pp. 367–372 (1982).
Hallauer, et al, "Corn Breeding", Corn and Corn Improvement pp. 463–564 (1988).
Lowe, Keith. Patent Application 0 160 390.
Meghji, M.R., J.W. Dudley, R.J. Lambert, and G.F. Sprague. "Inbreeding Depression, Inbred and Hybrid Grain Yields, and Other Traits of Maize Genotypes Representing Three Eras". Corp science, vol. 24, pp. 545–549 (1984).
Phillips, et al., "Cell/Tissue Culture and In Vitro Manipulation". In Corn & Corn Improvement, 3rd Ed., ASA Publication, #18, pp. 345–349 & 356–357 (1988).
Poehlman, John Milton. Breeding Field Crop, AVI Publishing Company, Inc., Westport, Connecticut, pp. 237–246 (1987).
Rao, K.V., et al., "Somatic Embryogenesis in Glume Callus Cultures", Osmania University, Hyberabad, India.
Sass (1977) "Morphology". In Corn & Corn Improvement. ASA Publication, Madison, WI, pp. 89–109.
Songstad, David D., David R. Duncan, and Jack M. Widholm. "Effect of 1–aminocyclopropane–1–carboxylic acid, silver nitrate, and norbornadiene on plant regeneration form maize callus cultures", Plant Cell Reports, 7:262–265 (1988).
Tomes, et al, "the Effect of Parental Genotype on Initiation of Embryogenic Callus from Elite Maize (Zea mays I.) Germplasm". Theor. Appl. Genet. 70., pp. 505–509, (1985).
Troyer, et al., "Selection for Early Flowering in Corn: 10 Late Synthetics". Crop Science, vol. 25, pp. 695–697 (1985).
Umbeck, et al. "Reversion of Male–Sterile T–Cytoplasm Maize to Male Fertility in Tissue Culture", Crop Science vol. 23, pp. 584–588 (1983).
Wright, H., "Commercial Hybrid Seed Production", Hybridization of Crop Plants, pp. 161–176, (1980).
Wych, R.D., "Production of Hybrid Seed Corn"; Corn and Corn Improvement, pp. 565–607 (1988).

*Primary Examiner*—Gary Benzion
*Attorney, Agent, or Firm*—Dana Rewoldt

[57] ABSTRACT

Broadly this invention provides inbred corn line ZS01219. The methods for producing a corn plant by crossing the inbred line ZS01219 are encompassed by the invention. Additionally, the invention relates to the various parts of inbred ZS01219 including culturable cells. This invention relates to hybrid corn seeds and plants produced by crossing the inbred line ZS01219 with at least one other corn line.

12 Claims, No Drawings

5,763,754

INBRED CORN LINE ZS01219

FIELD OF THE INVENTION

This invention is in the field of corn breeding, specifically relating to an inbred corn line designated ZS01219.

BACKGROUND OF THE INVENTION

The original maize plant was indigenous to the Western Hemisphere. The plants were weedlike and only through the efforts of early breeders was a cultivated crop species developed. The physical traits of maize are such that self pollination or cross pollination can occur. Each plant has a separate male and female flower, the tassel and ear, respectively. Natural pollination occurs when wind transfers pollen from tassel to the silks on the corn ears. This type of pollination contributed to the wide variation of maize varieties present in the Western Hemisphere.

The development of a planned breeding program for maize only occurred in the last century. Originally, maize was an open pollinated variety having heterogeneous genotypes. The maize farmer selected uniform ears from the yield of these genotypes and reserved them for planting the next season. The result was a field of maize plants that were segregating for a variety of traits. This type of maize selection lead to at most incremental increases in seed yield.

Large increases in seed yield were the result of the development of hybrid corn varieties in planned breeding programs. Hybrids were developed by selecting corn lines and selfing these lines for several generations to develop homozygous pure inbred lines and crossing selected inbred lines with unrelated inbred lines to produce hybrid progeny (F1). Inbred lines can be difficult to produce since the inbreeding process in corn decreases the vigor. However, when two inbred lines are crossed, the hybrid plant evidences greatly increased vigor compared to open pollinated segregating maize plants. An important factor of the homozygosity and the homogeneity of the inbred lines is that the hybrid from any cross will always be the same, and can be reproduced.

The ultimate objective of the commercial maize seed companies is to produce high yielding, agronomically sound plants which perform well in certain regions or areas of the Corn Belt. To produce these types of hybrids, the companies must develop inbreds which carry needed traits into the hybrid combination. Hybrids are not uniformly adapted for the Corn Belt, but are specifically adapted for regions of the Corn Belt. Northern regions of the Corn Belt require shorter season hybrids than do southern regions of the Corn Belt. Hybrids that grow well in Colorado and Nebraska soils may not flourish in rich Illinois soil. Thus, a variety of major agronomic traits are important in hybrid combination for the various Corn Belt regions, and have an impact on hybrid performance.

Inbred line development and hybrid testing have been emphasized in the past half century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcross populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include yield potential in hybrid combination; dry down; maturity; grain moisture at harvest; greensnap; resistance to root lodging; resistance to stalk lodging; grain quality; disease and insect resistance; ear and plant height; performance in different soil types such as: low level of organic matter, clay, sand, black, high pH, low pH; performance in: wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. Thus, the general procedure of producing a non segregating $F_1$ generation and self pollinating to produce a $F_2$ generation that segregates for traits does not easily lead to a useful inbred. Great care and breeder expertise must be used in selection of breeding material to continue to increase yield and agronomics of inbreds and resultant commercial hybrids.

SUMMARY OF THE INVENTION

The present invention relates to an inbred corn line ZS01219. Specifically, this invention relates to plants and seeds of this line. Additionally, this relates to a method of producing hybrid seed corn from this inbred. More particularly, this invention relates to the unique combination of traits that combine in corn line ZS01219.

Generally then, broadly the present invention includes an inbred corn seed designated ZS01219. This seed produces a corn plant.

The invention also includes the tissue culture of regenerable cells of ZS01219 wherein the tissue regenerates plants having the genotype of ZS01219. The tissue culture is selected from the group consisting of leaves, pollen, embryos, roots, root tips, anthers, silk, flowers, kernels, ears, cobs, husks and stalks, and cells and protoplasts thereof. The corn plant regenerated from ZS01219 having ZS01219's genotype.

The invention extends to hybrid seed produced by planting, in pollinating proximity, seeds of corn inbred lines ZS01219 and another inbred line; cultivating corn plants resulting from said planting; preventing pollen production by the plants of one of the inbred lines; allowing natural cross pollinating to occur between said inbred lines; and harvesting seeds produced on plants of the inbred. The hybrid seed produced by hybrid combination of plants of inbred corn seed designated ZS01219 and plants of another inbred line. Hybrid plants grown from this hybrid seed.

The invention further includes a method of hybrid F1 production. A first generation (F1) hybrid corn plant produced by the process of planting, in pollinating proximity, seeds of corn inbred lines ZS01219 and another inbred line; cultivating corn plants resulting from said planting; preventing pollen production by the plants of one of the inbred lines; allowing natural cross pollinating to occur between said inbred lines; harvesting seeds produced on plants of the inbred; and growing a harvested seed.

A tissue culture of the regenerable cells of hybrid plants produced with use of ZS01219 genetic material. A tissue culture of the regenerable cells of the corn plant produced by the method described above.

DEFINITIONS

In the description and examples which follow, a number of terms are used. In order to provide a clear and consistent understanding of the specifications and claims, including the scope to be given such terms, the following definitions are provided.

BL MOIST

The moisture percentage of the grain at black layer, i.e., when 50% of the plants per plot have reached physiological maturity.

COLD GERM

Cold Germ is a measurement of seed germination under cold soil conditions. Data is reported as percent of seed germinating.

ECB

European corn borer a maize eating insect. ECBI is the first brood generation of European corn borers. ECBII is the second generation of European corn borers.

EMERGE

The number of emerged plants per plot (planted at the same seedling rate) collected when plants have two fully developed leaves.

GI

This is a selection index which provides a single quantitative measure of the worth of a hybrid based on four traits. Yield is the primary trait contributing to index values. The GI value is calculated by combining stalk lodging, root lodging, yield and dropped ears according to the attached mathematical formula:

$$GI = 100 + 0.5(YLD) - 0.9(\% \text{ STALK LODGE}) - 0.9(\% \text{ ROOT LODGE}) - 2.7(\% \text{ DROPPED EAR})$$

GLS

Gray Leaf Spot (Cercospora Zeae) disease rating. This is rated on a 1–9 scale with a "1" being very susceptible, and a "9" being very resistant.*

GW

Goss' Wilt (*Corynebacterium nebraskense*). This is rated on a 1–9 scale with a "1" being very susceptible, and a "9" being very resistant.*

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(\text{Max Temp (°F.)} + \text{Min Temp (°F.)})}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain which has reached physiological maturity (black layer).

HEATPEEK

The number of GDU's after planting of an inbred when approximately 50 percent of the plants show visible tassel extension.

HEATP50 or HTP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The corn is rated on a 1–9 scale with a "1" being very susceptible, and a "9" being very resistant.*

$MDMV_B$

Maize Dwarf Mosaic Virus strain B. This is rated on a 1–9 scale with a "1" being very susceptible and a "9" being very resistant.*

MOISTURE

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

PCT TILLER

The total number of tillers per plot divided by the total number of plants per plot.

PLANT

This term includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

PLANT HEIGHT

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

SHED

The volume of pollen shed by the male flower rated on a 1–9 scale where a "1" is a very light pollen shedder, a "4.5" is a moderate shedder, and a "9" is a very heavy shedder. If the Table(s) 3 have reduced the 1–9 shed scale to a 1–3 shed scale then any shed on Table 3 can be multiplied by 3 to reach the 1–9 shed scale.

SLB

Southern Leaf Blight (*Bipolaris maydis*) disease rating. This is rated on a 1–9 scale with a "1" being very susceptible, and a "9" being very resistant.*

TWT

The measure of the weight of grain in pounds for a one bushel volume adjusted for percent grain moisture.

VIGOR

Visual rating of 1 to 9 made 2–3 weeks post-emergence where a "1" indicates very poor early plant development, and a "9" indicates superior plant development.

WARM GERM

A measurement of seed germination under ideal (warm, moist) conditions. Data is reported as percent of seeds germinating.

YIELD (YLD)

Actual yield of grain at harvest adjusted to 15.5% moisture. Measurements are reported in bushels per acre.

% DROPPED EARS (DE)

The number of plants per plot which dropped their primary ear divided by the total number of plants per plot.

% LRG FLAT

Percentage by weight of shelled corn that passes through a $26/64$ inch round screen and a $14/64$ inch slot screen, but does not pass through a screen with $20.5/64$ inch round openings.

% LRG ROUND

Percentage by weight of shelled corn that passes through a $26/64$ inch round screen, but does not pass through a $14/64$ inch slot screen or a screen with $20.5/64$ inch round openings.

% MED FLAT

Percentage by weight of shelled corn that passes through a $20.5/64$ inch round screen and a $13/64$ inch slotted screen, but does not pass through a screen with $17/64$ inch round openings.

% MED ROUND

Percentage by weight of shelled corn that passes through a $20.5/64$ inch round screen, but does not pass through a $13/64$ inch slot screen or a screen with $17/64$ inch round openings.

% SML FLAT

Percentage by weight of shelled corn that passes through a $17/64$ inch round screen and a $12/64$ inch slotted screen, but does not pass through a screen with $15/64$ inch round openings.

% SML ROUND

Percentage by weight of shelled corn that passes through a $17/64$ inch round screen, but does not pass through a $12/64$ inch slotted screen or a screen with $15/64$ inch round openings.

% ROOT LODGE (RL)

Percentage of plants per plot leaning more that 30 degrees from vertical divided by total plants per plot.

% STALK LODGE (SL)

Percentage of plants per plot with the stalk broken below the primary ear node divided by the total plants per plot.

* Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

ZS01219 can be best used as a female line due to its seed production abilities. This ZS01219 line evidences good general combining ability and specific combining ability with many types of males.

The inbred has shown uniformity and stability within the limits of environmental influence for all the traits as described in the Variety Description Information (Table 1) that follows. Most of the data in the Variety Description information was collected at Slater, Iowa.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in ZS01219.

The best method of producing the invention, ZS01219 which is substantially homozygous, is by planting the seed of ZS01219 which is substantially homozygous and self-pollinating or sib pollinating the resultant plant in an isolated environment, and harvesting the resultant seed or the resultant pollen.

TABLE 1

| ZS01219 VARIETY DESCRIPTION INFORMATION | |
|---|---|
| #1 | Type: Dent |
| #2 | Region Best Adapted: Southern Minnesota, northern Iowa, southern Wisconsin and southern Michigan regions |

| INBRED | CG:ZS01219 | |
|---|---|---|
| #3 | MATURITY | |
| DAYS | HEATUNITS | |
| 71 | 1427 | FROM PLANTING TO 50% OF PLANTS IN SILK |
| 70 | 1410 | FROM PLANTING TO 50% OF PLANTS IN POLLEN |
| 3 | | FROM 10% TO 90% POLLEN SHED |
| #4 | PLANT | |
| DATA | | |
| 4 | | ANTHOCYANIN OF BRACE ROOTS: 1=ABSENT 2=FAINT 3=MODERATE 4=DARK |

-continued

| #5 | LEAF COLOR/DATA | |
|---|---|---|
| | 3/DARK GREEN | LEAF COLOR **MUNSELL CODE-5GY 3/4 |
| | 5 | LEAF SHEATH PUBESCENCE (1=NONE TO 9=PEACH FUZZ) |
| | 4 | MARGINAL WAVES (1=NONE TO 9=MANY) |
| | 5 | LONGITUDINAL CREASES (1=NONE TO 9=MANY) |

| #6 | TASSEL COLOR/DATA | |
|---|---|---|
| | 7 | POLLEN SHED (0=STERILE TO 9=HEAVY SHEDDER) |
| | 11/PINK | ANTHER COLOR **MUNSELL CODE-5R 7/4 |
| | 1&17/L.GRN/PUR | GLUME COLOR **MUNSELL CODE-2.5GY 7/6 w/s 5R 4/8 |
| | 2 | BAR GLUME: 1=ABSENT 2=PRESENT |

| #7A | EAR (UNHUSKED DATA) COLOR/DATA | |
|---|---|---|
| | 14/RED | SILK COLOR (3 DAYS AFTER EMERGE) **MUNSELL CODE-5R 4/8 |
| | 2/MEDIUM GREEN | FRESH HUSK (25 DAYS AFTER 50% SILK) **MUNSELL CODE-5GY 6/6 |
| | 22/TAN | DRY HUSK COLOR (65 DAYS AFTER 50% SILK **MUNSELL CODE-2.5Y 7/4 |
| | 1 | POSITION OF EAR AT DRY HUSK: 1=UPRIGHT 2=HORIZONTAL 3=PENDENT |
| | 5 | HUSK TIGHTNESS (1=VERY LOOSE TO 9=VERY TIGHT) |
| | 2 | HUSK EXTENSION AT HARVEST: 1=EXPOSED EAR 2=8CM 3=8–10CM 4=>10CM |

| #7B | EAR (HUSKED DATA) DATA | |
|---|---|---|
| | 2 | KERNEL ROWS: 1=INDISTINCT 2=DISTINCT |
| | 2 | ROW ALIGNMENT: 1=STRAIT 2=SLIGHT CURVE 3=SPIRAL |
| | 1 | EAR TAPPER: 1=STRAIT 2=AVERAGE 3=EXTREME |

| #8 | KERNEL (DRY) COLOR/DATA | |
|---|---|---|
| | 1 | ALEURONE COLOR PATTERN: 1=HOMO 2=SEG |
| | 8/YELLOW-ORNGE | ALEURONE COLOR **MUNSELL CODE-7.5YR 7/10 |
| | 8/YELLOW-ORNGE | HARD ENDOSPERM COLOR **MUNSELL CODE-5Y 6/8 |
| | . | ENDOSPERM TYPE |
| | 7/YELLOW | CROWN COLOR **MUNSELL CODE-2.5Y 8/10 |

| #9 | COB COLOR | |
|---|---|---|
| | 12/LIGHT RED | COB COLOR **MUNSELL CODE-10R 4/6 |

PROJECT CG PVP TRAITS
INBRED ZS01219

| #10 | N | MEAN | STD. | T-STAT | PROB | 95% CI |
|---|---|---|---|---|---|---|
| EAR HEIGHT (CM) | 15 | 75.87 | 9.71 | 30.26 | 0.0000 | (70.95, 80.78) |
| LENGTH OF PRIMARY EAR LEAF (CM) | 15 | 77.31 | 3.71 | 80.69 | 0.0000 | (75.43, 79.18) |
| WIDTH OF PRIMARY EAR LEAF (CM) | 15 | 8.53 | 0.46 | 72.45 | 0.0000 | (8.30, 8.76) |
| TOP EAR INTERNODE (CM) | 15 | 15.40 | 1.05 | 57.05 | 0.0000 | (14.87, 15.93) |
| DEGREE OF LEAF ANGLE | 15 | 34.33 | 5.30 | 25.09 | 0.0000 | (31.65, 37.02) |
| # OF EARS PER PLANT | 15 | 1.00 | 0.00 | | | (1.00, 1.00) |
| # OF LEAVES ABOVE TOP EAR | 15 | 6.27 | 0.46 | 53.02 | 0.0000 | (6.04, 6.50) |
| # OF PRIMARY LATERAL TASSEL BRANCHES | 15 | 10.87 | 1.60 | 26.34 | 0.0000 | (10.06, 11.68) |
| PLANT HEIGHT (CM) | 15 | 223.8 | 8.31 | 104.3 | 0.0000 | (219.6, 228.0) |
| TASSEL LENGTH (CM) | 15 | 28.65 | 1.58 | 70.29 | 0.0000 | (27.85, 29.45) |
| TASSEL BRANCH ANGLE | 15 | 22.33 | 7.76 | 11.14 | 0.0000 | (18.41, 26.26) |
| # OF TILLER PER PLANTS | 15 | 0.33 | 0.62 | 2.09 | 0.0552 | (0.02, 0.65) |
| WEIGHT PER 100 KERNELS (GM) | 15 | 36.63 | 2.69 | 52.69 | 0.0000 | (35.27, 38.00) |
| EAR LENGTH (CM) | 15 | 16.73 | 2.09 | 30.94 | 0.0000 | (15.67, 17.79) |
| EAR WEIGHT (GM) | 15 | 117.2 | 23.98 | 18.94 | 0.0000 | (105.1, 129.4) |
| # OF KERNEL ROWS | 15 | 14.00 | 1.07 | 50.72 | 0.0000 | (13.46, 14.54) |
| COB DIAMETER AT MID-POINT (MM) | 15 | 27.13 | 1.60 | 65.78 | 0.0000 | (26.32, 27.94) |
| EAR DIAMETER AT MID-POINT (MM) | 15 | 42.67 | 2.53 | 65.42 | 0.0000 | (41.39, 43.95) |
| KERNEL LENGTH (MM) | 15 | 10.33 | 0.62 | 64.84 | 0.0000 | (10.02, 10.65) |
| KERNEL THICKNESS (MM) | 15 | 5.53 | 0.83 | 25.70 | 0.0000 | (5.11, 5.96) |
| KERNEL WIDTH (MM) | 15 | 9.47 | 0.64 | 57.29 | 0.0000 | (9.14, 9.79) |
| % ROUND KERNELS (SHAPE GRADE) | 15 | 44.33 | 22.59 | 7.60 | 0.0000 | (32.90, 55.76) |
| SHANK LENGTH | 15 | 10.80 | 4.31 | 9.70 | 0.0000 | (8.62, 12.98) |

11 DISEASE RESISTANCE - Northern leaf blight = 1
NLSr2* = 9
Gray leaf spot = 6
Eye = 8
GW = 2.5
MDMVB = 8

*Northern Leaf Spot Race Two
12 Other comparable inbreds are ZS0986 (PVP 9200041), ZS1202, and A632.

The Munsell code is a reference book of color which is known and used in the industry and by persons with ordinary skill in the art of plant breeding.

The purity and homozygosity of inbred ZS01219 is constantly being tracked using isozyme genotypes as shown in Table 2.

Isozyme Genotypes for ZS01219

Isozyme data were generated for inbred corn line ZS01219 according to procedures known and published in the art. The data in Table 2 gives the electrophoresis data on ZS01219.

and vigor of ZS01219 is significantly greater. ZS01219 has early male flowering as evidenced by the significantly fewer GDU's for HEATPEEK and all HEATP ratings. Moisture of grain at harvest is significantly greater for ZS0986. While germination ratings under both warm and cold conditions are significantly less than ZS0986, they are acceptable. ZS01219 produces a significantly greater percent of large and medium round kernel sizes.

TABLE 2

| ELECTROPHORESIS RESULTS FOR ZS01219 | | | | | | | | | |
|---|---|---|---|---|---|---|---|---|---|
| INBRED | ACP1 | ACP4 | ADH | MDH1 | MDH2 | PGD1 | PGD2 | PH1 | PGM | IDH2 |
| ZS01219 | 11 | 00 | 22 | 22 | 22 | 11 | 11 | 22 | 22 | 11 |

TABLE 3A

| PAIRED INBRED COMPARISON DATA | | | | | | | | | |
|---|---|---|---|---|---|---|---|---|---|
| YEAR | INBRED | VIGOR | EMERGE | PCT TILLER | PLANT HEIGHT | EAR HEIGHT | SHED | EAR QUALITY | PCT BARREN |
| OVERALL | ZS01219 | 6.4 | 89.7 | | 154.5 | 59.1 | 5.4 | 2.7 | |
| | ZS0986 | 5.5 | 79.1 | | 145.4 | 78.5 | 6.0 | 2.8 | |
| | # EXPTS | 13 | 13 | | 13 | 13 | 11 | 3 | |
| | DIFF | 0.9 | 10.6 | | 9.2 | 19.4 | 0.6 | 0.2 | |
| | PROB | 0.013** | 0.020** | | 0.010** | 0.000* | 0.111 | 0.423 | |

| YEAR | INBRED | HEATP10 | HEATP50 | HEATP90 | HEATS10 | HEATS50 | HEATS90 |
|---|---|---|---|---|---|---|---|
| OVERALL | ZS01219 | 1387 | 1424 | 1510 | 1437 | 1468 | 1511 |
| | ZS0986 | 1428 | 1467 | 1546 | 1436 | 1474 | 1516 |
| | # EXPTS | 13 | 13 | 13 | 13 | 13 | 13 |
| | DIFF | 41 | 43 | 37 | 1 | 6 | 5 |
| | PROB | 0.000* | 0.001* | 0.004* | 0.942 | 0.575 | 0.696 |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS01219 | 1350 | 2430 | 32.6 | | | | 12.1 | 52.1 |
| | ZS0986 | 1395 | 2488 | 30.5 | | | | 11.1 | 51.1 |
| | # EXPTS | 13 | 2 | 2 | | | | 13 | 13 |
| | DIFF | 45 | 58 | 2.1 | | | | 1.0 | 1.0 |
| | PROB | 0.000* | 0.148 | 0.111 | | | | 0.012** | |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | ZS01219 | 95.3 | 85.4 | 6.0 | 6.8 | 39.0 | 32.4 | 9.3 | 3.8 |
| | ZS0986 | 97.5 | 93.9 | 2.2 | 10.2 | 23.6 | 45.1 | 7.0 | 7.4 |
| | # EXPTS | 13 | 13 | 13 | 13 | 13 | 13 | 13 | 13 |
| | DIFF | 2.2 | 8.5 | 3.8 | 3.5 | 15.4 | 12.7 | 2.4 | 3.5 |
| | PROB | 0.001* | 0.002* | 0.001* | 0.115 | 0.000* | | | |

Inbred and Hybrid Performance of ZS01219

The traits and characteristics of inbred corn line ZS01219 are listed to compare with other inbreds and/or in hybrid combination. ZS01219 data shows the characteristics and traits of importance, giving a snapshot of ZS01219.

Table 3A shows a comparison between ZS01219 and ZS0986. ZS01219 is a significantly taller plant than ZS0986 but has significantly lower ear height. Seedling emergence Table 3B compares ZS01219 with A632. ZS01219 has significantly lower ear height than A632, and significantly greater seedling emergence and vigor. Pollen shed is significantly less, but acceptable. ZS01219 is a later maturity line as evidenced by the significantly greater GDU's at HEATPEEK, all HEATP ratings and the HEATS10 and HEATS50 ratings, and the significantly greater grain moisture at harvest. ZS01219 produces significantly greater percent of large flat and round kernel sizes, and significantly fewer medium round sizes.

TABLE 3B

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS01219 | 6.2 | 89.0 | | 161.2 | 63.9 | 5.4 | 2.7 | |
| | A632 | 5.5 | 79.7 | | 159.2 | 72.3 | 6.4 | 2.7 | |
| | # EXPTS | 12 | 12 | | 12 | 12 | 11 | 3 | |
| | DIFF | 0.8 | 9.3 | | 2.0 | 8.4 | 1.0 | 0.0 | |
| | PROB | 0.028** | 0.011** | | 0.573 | 0.010* | 0.025** | | |

| YEAR | INBRED | HEATP10 | HEATP50 | HEATP90 | HEATS10 | HEATS50 | HEATS90 |
|---|---|---|---|---|---|---|---|
| OVERALL | ZS01219 | 1393 | 1432 | 1511 | 1438 | 1469 | 1503 |
| | A632 | 1364 | 1410 | 1494 | 1404 | 1449 | 1489 |
| | # EXPTS | 12 | 12 | 12 | 12 | 12 | 12 |
| | DIFF | 29 | 22 | 17 | 34 | 20 | 14 |
| | PROB | 0.021** | 0.058*** | 0.081*** | 0.020** | 0.061*** | 0.190 |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS01219 | 1350 | 2460 | 32.1 | | | | 11.9 | 64.3 |
| | A632 | 1262 | 2497 | 30.7 | | | | 11.3 | 44.6 |
| | # EXPTS | 12 | 3 | 3 | | | | 12 | 12 |
| | DIFF | 88 | 37 | 1.4 | | | | 0.6 | 19.7 |
| | PROB | 0.000* | 0.174 | 0.512 | | | | 0.085*** | |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | ZS01219 | 95.8 | 87.5 | 8.6 | 7.8 | 39.0 | 30.1 | 8.8 | 3.4 |
| | A632 | 96.9 | 86.6 | 4.7 | 3.9 | 42.6 | 28.0 | 12.2 | 5.5 |
| | # EXPTS | 12 | 12 | 12 | 12 | 12 | 12 | 12 | 12 |
| | DIFF | 1.1 | 0.8 | 3.9 | 3.9 | 3.7 | 2.1 | 3.4 | 2.1 |
| | PROB | 0.057*** | 0.725 | 0.014** | 0.000* | 0.043** | | | |

Table 3C is an inbred comparison between ZS01219 and ZS1202. ZS01219 is significantly shorter in plant height and ear height than ZS1202. Seedling vigor is significantly less, but emergence and pollen shed is significantly greater than ZS1202. ZS01219 has significantly fewer GDU's to all HEATP ratings, and to HEATS50. Grain moisture at harvest of ZS01219 is significantly greater than ZS1202. ZS01219 produces significantly less large seed sizes and significantly more medium round kernel sizes than ZS1202.

TABLE 3C

PAIRED INBRED COMPARISON DATA

| YEAR | INBRED | VIGOR | EMERGE | PCT TILLER | PLANT HEIGHT | EAR HEIGHT | SHED | EAR QUALITY | PCT BARREN |
|---|---|---|---|---|---|---|---|---|---|
| OVERALL | ZS01219 | 6.4 | 89.8 | | 166.3 | 66.0 | 5.8 | 2.7 | |
| | ZS1202 | 6.9 | 82.0 | | 177.9 | 81.5 | 4.9 | 2.3 | |
| | # EXPTS | 28 | 28 | | 26 | 28 | 26 | 3 | |
| | DIFF | 0.5 | 7.9 | | 11.6 | 15.5 | 0.9 | 0.3 | |
| | PROB | 0.041** | 0.000* | | 0.000* | 0.000* | 0.003* | 0.423 | |

| YEAR | INBRED | HEATP10 | HEATP50 | HEATP90 | HEATS10 | HEATS50 | HEATS90 |
|---|---|---|---|---|---|---|---|
| OVERALL | ZS01219 | 1387 | 1432 | 1529 | 1439 | 1474 | 1519 |
| | ZS1202 | 1406 | 1455 | 1554 | 1450 | 1491 | 1531 |
| | # EXPTS | 28 | 28 | 28 | 28 | 28 | 28 |
| | DIFF | 19 | 23 | 25 | 11 | 17 | 11 |
| | PROB | 0.007* | 0.002* | 0.001* | 0.198 | 0.045** | 0.333 |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS01219 | 1354 | 2455 | 32.1 | | | | 12.5 | 66.0 |
| | ZS1202 | 1349 | 2560 | 29.5 | | | | 11.6 | 56.2 |
| | # EXPTS | 28 | 4 | 3 | | | | 28 | 28 |
| | DIFF | 5 | 105 | 2.6 | | | | 0.9 | 9.8 |
| | PROB | 0.613 | 0.103 | 0.378 | | | | 0.021** | |

TABLE 3C-continued

| | | PAIRED INBRED COMPARISON DATA | | | | | | | |
|---|---|---|---|---|---|---|---|---|---|
| YEAR | INBRED | WARM GERM | COLD GERM | % LRG ROUND | % LRG FLAT | % MED ROUND | % MED FLAT | % SML ROUND | % SML FLAT |
| OVERALL | ZS01219 | 94.7 | 84.8 | 10.1 | 8.6 | 40.4 | 27.9 | 8.4 | 2.9 |
| | ZS1202 | 94.7 | 85.5 | 26.0 | 23.7 | 23.4 | 21.3 | 2.6 | 1.6 |
| | # EXPTS | 26 | 26 | 28 | 28 | 28 | 28 | 27 | 27 |
| | DIFF | 0.1 | 0.7 | 15.9 | 15.1 | 17.0 | 6.6 | 5.7 | 1.3 |
| | PROB | 0.919 | 0.783 | 0.000* | 0.000* | 0.000* | | | |

Table 4 shows the GCA (general combining ability) estimates of ZS01219 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids, particularly the leader in the industry and ICI Seeds' commercial products and pre-commercial hybrids which were grown in the same sets and locations.

Table 4A shows ZS01219 crossed in 1456 hybrid combinations. ZS01219 shows a positive advantage for both percent stalk and root lodging.

ZS1202, ZS01219 shows less favorable yield or moisture advantage, but shows positive advantage for stalk and root lodging compared to a negative value for ZS1202.

TABLE 4B

| | | N | FI | YM | GI | I | YLD | MST |
|---|---|---|---|---|---|---|---|---|
| ZS0986 | XR = | 1152 | -3.1 | -0.3 | -3.7 | -2.5 | -4.4 | 0.2 |
| A632 | XR = | 213 | -3.4 | -0.3 | -2.9 | -2.5 | -4.4 | -0.3 |
| ZS1202 | XR = | 1635 | -0.7 | 0.1 | -1.5 | -0.7 | -1.4 | 0.4 |

| | | % SL | % RL | % DE | TWT | POP | RM |
|---|---|---|---|---|---|---|---|
| ZS0986 | XR = | -0.7 | -0.9 | 0.0 | 0.8 | -91 | 107 |
| A632 | XR = | 0.1 | -0.6 | -0.0 | -0.8 | -510 | 98 |
| ZS1202 | XR = | -0.2 | -0.7 | 0.0 | -0.7 | -256 | 110 |

Table 5A shows in the advantage the ZS01219 hybrid has over three commercially available ICI Seeds' hybrids. The

TABLE 4A

GCA & SCA ESTIMATES

| | ADVANTAGES OVER COMMERCIALS & N'S | | | | | | | | | | | | | | | | ENT ZS01219 |
|---|---|---|---|---|---|---|---|---|---|---|---|---|---|---|---|---|---|
| | N93 | N94 | N95 | N | FI | YM | GI | I | YLD | MST | % SL | % RL | % DE | TWT | POP | RM |
| XR = | 490 | 155 | 775 | 1456 | -2.0 | -0.4 | -0.6 | -1.4 | -2.5 | -0.6 | 0.3 | 0.4 | -0.0 | -0.0 | -186 | 108 |
| XH = | | | | 120 | -3.9 | -0.7 | -2.0 | -2.3 | -5.7 | -0.8 | 0.6 | 0.4 | -0.0 | 0.0 | -238 | 110 |
| XT = | | | | 35 | -0.3 | -0.2 | 0.5 | 0.8 | -0.4 | -0.3 | 0.2 | 0.4 | 0.0 | -0.0 | -186 | 109 |

XR = GCA ESTIMATE: WEIGHTED BY EXPT
XH = GCA ESTIMATE: WEIGHTED BY PARENT2
XT = SAME AS XH, BUT USING ONLY THOSE PARENT2 WITH TWO YEARS OF DATA

Table 4B compares ZS01219 in random hybrid combinations with ZS0986, A632 and ZS1202 in random combinations. Compared to ZS0986 and A632, ZS01219 has comparable or better advantage for all traits. Yield of ZS01219 at -2.5 is better than -4.4 for ZS0986 and A632, and stalk and root lodging show positive advantage. Compared to ZS01219 hybrid is of comparable maturity and yield level as 8541. It shows a significant maturity (moisture) advantage over 8543 and has comparable or better yield levels. ZS01219 hybrid is later in maturity than 8570 and shows a significantly yield advantage. Stalk and root lodging of all hybrids are at similar comparative and acceptable levels.

TABLE 5A

HYBRID SUMMARY ZS01219/INBRED

| HYBRID | TYPE | # | GI | ADV | FI | ADV | YLD | ADV | MOIST | ADV | SL | ADV | RL | ADV | DE | ADV | TWT | ADV | POP | ADV |
|---|---|---|---|---|---|---|---|---|---|---|---|---|---|---|---|---|---|---|---|---|
| ZS01219 | R | 5 | 175 | 5 | 115 | 2 | 160.7 | 8.1* | 26.0 | -1.0 | 3.9 | 0.4 | 0.0 | 0.4 | 0.8 | -0.0 | 49.6 | 0.8 | 26310 | -261 |
| 8570 | R | 5 | 170 | | 113 | | 152.6 | | 25.0 | | 4.3 | | 0.4 | | 0.7 | | 48.8 | | 26572 | |
| ZS01219 | R | 5 | 175 | -1 | 115 | 3 | 160.7 | 3.0 | 26.0 | 1.6* | 3.9 | -1.6 | 0.0 | 0.3 | 0.8 | -0.6 | 49.6 | 1.4 | 26310 | 0 |
| 8543 | R | S | 176 | | 112 | | 157.7 | | 27.6 | | 2.3 | | 0.3 | | 0.2 | | 48.3 | | 26310 | |
| ZS01219 | R | S | 175 | -2 | 115 | -2 | 160.7 | 0.3 | 26.0 | 0.3 | 3.9 | -1.6 | 0.0 | 0.1 | 0.8 | -0.5 | 49.6 | 1.1 | 26310 | -87 |
| 8541 | R | 5 | 177 | | 117 | | 160.4 | | 26.3 | | 2.4 | | 0.1 | | 0.3 | | 48.6 | | 26397 | |

Table 6A shows the entomology strengths and weaknesses of the inbred.

TABLE 6A

| INBRED | ECB1 RATING | ECB2 RATING | EAR DAMAGE RATING | PLANT INTEGRITY RATING |
|---|---|---|---|---|
| ZS01219 | 5.7 | 4.8 | 2 | 5.9 |

The inbred ZS01219 can be employed as the female plant in a hybrid production field. This inbred is a medium height line with moderately low ear height. ZS01219 has a light green leaf color and good disease resistance. In hybrid combination, ZS01219 shows good resistance to stalk and root lodging. In the areas to which its hybrids are adapted, yield performance is very good and the hybrids move north in their adapted zones very well. The inbred ZS01219 has good disease resistance which it transmits to its hybrids. The inbred ZS01219 has good GCA and SCA with many types of male lines.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line ZS01219. Further, both first and second parent corn plants can come from the inbred corn line ZS01219. A variety of breeding methods can be selected depending on the mode of reproduction, the trait, the condition of the germplasm. Thus, any such methods using the inbred corn line ZS01219 are part of this invention: selfing, backcrosses, hybrid production, crosses to populations, haploid and anther culturing and the like.

Various culturing techniques known to those skilled in the art, such as haploid, transformation, and a host of other conventional and unconventional methods are within the scope of the invention. All plants and plant cells produced using inbred corn line ZS01219 are within the scope of this invention. The invention encompasses the inbred corn line used in crosses with other, different, corn inbreds to produce (F1) corn hybrid seeds and plants with the characteristics that make good hybrids. This invention includes cells which upon growth and differentiation produce corn plants having the physiological and morphological characteristics of the inbred line ZS01219.

Duncan, from at least 1985–1988 produced literature on plant regeneration from callus. Both inbred and hybrid callus have resulted in regenerated plants at excellent efficiency rates. Somatic embryogenesis has been performed on various maize tissue such as glume which before the 1980's was considered unusable for this purpose. The prior art clearly teaches the regeneration of plants from various maize tissues.

European Patent Application, publication 160,390, describes tissue culture of corn which can be used by those skilled in the art. Corn tissue culture procedures are also described in the literature as early as 1982.

A deposit of at least 2500 seeds of the inbred seed of this invention is maintained by ICI Seeds, 2369 330th Street, Slater, Iowa 50244. Access to this deposit will be available during the pendency of this application to the Commissioner of Patents and Trademarks and persons determined by the Commissioner to be entitled thereto upon request. The deposit of at least 2500 seeds will be from the same inbred seed taken from the deposit maintained by ICI Seeds. The ATCC deposit will be maintained in that depository, which is a public depository, for a period of 30 years, or 5 years after the last request, or for the effective life of the patent, whichever is longer, and will be replaced if it becomes nonviable during that period.

Inbreds designated MBS are available from Mike Brayton Seed in Iowa. Inbreds designated SGI are available from Seed Genetic Inc. in New Jersey. Information on some ZS designations may be available from the PVP office.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. Inbred corn seed designated ZS01219, some of said seed deposited in the ATCC and carry accession number, 209107.

2. A corn plant produced by the seed of claim 1.

3. A tissue culture of regenerable cells of ZS01219 of claim 1 wherein the cells of the tissue culture regenerates plants comprising the phenotype of ZS01219.

4. A tissue culture according to claim 3, the tissue culture selected from the group consisting of leaves, pollen, embryos, roots, root tips, anthers, silk, flowers, kernels, ears, cobs, husks and stalks, and cells and protoplasts thereof.

5. A corn plant comprising the phenotype of ZS01219 regenerated from the cells of the tissue culture of claim 3.

6. Hybrid seed produced by:
 (a) planting, in pollinating proximity, seeds according to claim 1 of corn inbred lines ZS01219 and another inbred line, one of said inbred lines not releasing pollen;
 (b) cultivating corn plants resulting from said planting;
 (c) allowing natural cross pollinating to occur between said inbred lines; and
 (d) harvesting seeds produced on the non pollen releasing inbred.

7. Hybrid seed produced by hybrid combination of plants of inbred corn seed designated ZS01219 in claim 1 and plants of another inbred line.

8. Hybrid plants grown from seed of claim 7.

9. A first generation (F1) hybrid corn plant produced by using ZS01219 according to claim 1 the process of:

(a) planting, in pollinating proximity, seeds of corn inbred lines ZS01219 and another inbred line;

(b) cultivating corn plants resulting from said planting;

(c) preventing pollen production by the plants of one of the inbred lines;

(d) allowing natural cross pollinating to occur between said inbred lines;

(e) harvesting seeds produced on plants of the inbred line of step (c); and (f) growing a harvested seed of step (e).

10. A tissue culture of the regenerable cells of the corn plant of claim 8.

11. A tissue culture of the regenerable cells of the corn plant of claim 9.

12. An inbred corn plant with all the phenotypic, physiological and morphological characteristics of inbred corn line of claim 2.

* * * * *